US011737680B2

(12) United States Patent
Yellin et al.

(10) Patent No.: US 11,737,680 B2
(45) Date of Patent: Aug. 29, 2023

(54) EXTENDING THE TRACKING VOLUME IN A PROBE TRACKING SYSTEM

(71) Applicant: Biosense Webster (Israel) Ltd., Yokneam (IL)

(72) Inventors: Tamir Avraham Yellin, Yokneam Hamoshava (IL); Fares Safe, Yanuh (IL); Tamir Demri, Gilon (IL); Toam Shemesh, Hertziliya (IL); Daniel Osadchy, Haifa (IL); Dan Sztejnberg, Hertziliya (IL); Shaul Haim Raz, Shimshit (IL); Michael Maydel, Haifa (IL); Menachem Schechter, Kiryat Ata (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 1021 days.

(21) Appl. No.: 16/568,446

(22) Filed: Sep. 12, 2019

(65) Prior Publication Data

US 2020/0100700 A1    Apr. 2, 2020

Related U.S. Application Data

(60) Provisional application No. 62/740,012, filed on Oct. 2, 2018.

(51) Int. Cl.
*A61B 5/06* (2006.01)
*A61B 5/00* (2006.01)
(Continued)

(52) U.S. Cl.
CPC ............ *A61B 5/063* (2013.01); *A61B 5/6823* (2013.01); *A61B 5/6828* (2013.01);
(Continued)

(58) Field of Classification Search
CPC . A61B 2018/00577; A61B 18/14; A61B 5/68; A61B 5/287; A61B 18/1206; A61B 5/063
See application file for complete search history.

(56) References Cited

U.S. PATENT DOCUMENTS

| 6,690,963 B2 | 2/2004 | Ben Haim |
| 8,456,182 B2 | 6/2013 | Bar-Tal |
| (Continued) | | |

FOREIGN PATENT DOCUMENTS

| EP | 1757227 A2 | 2/2007 |
| EP | 2168478 A1 | 3/2010 |
| (Continued) | | |

OTHER PUBLICATIONS

European Search Report for corresponding EPA No. 19200731.8 dated Mar. 11, 2020.

*Primary Examiner* — Colin T. Sakamoto
(74) *Attorney, Agent, or Firm* — Notaro, Michalos & Zaccaria P.C.

(57) ABSTRACT

A system includes multiple electrically-conductive channels and a processor. The processor is configured to receive, over the electrically-conductive channels, (i) respective first electric currents from a probe, which is within a body of a patient, via a plurality of first electrodes, which are attached to skin of the patient at a region of the body, and (ii) a second electric current from the probe via a second electrode, which is attached to the skin and is connected to one of the channels. The processor is further configured to ascertain respective first electric-current values of the first electric currents and a second electric-current value of the second electric current, and to calculate a position of the probe between the region and the second electrode, based on the first electric-current values and the second electric-current value. Other embodiments are also described.

27 Claims, 14 Drawing Sheets

(51) Int. Cl.
    *A61B 18/12* (2006.01)
    *A61B 18/00* (2006.01)
(52) U.S. Cl.
    CPC .......... *A61B 5/6847* (2013.01); *A61B 5/6886* (2013.01); *A61B 18/1206* (2013.01); *A61B 2018/00577* (2013.01); *A61B 2018/00827* (2013.01); *A61B 2018/00922* (2013.01)

(56) References Cited

U.S. PATENT DOCUMENTS

| | | | | |
|---|---|---|---|---|
| 8,478,383 | B2* | 7/2013 | Bar-Tal | A61B 5/063 |
| | | | | 703/7 |
| 2007/0060832 | A1* | 3/2007 | Levin | A61B 5/053 |
| 2011/0105861 | A1* | 5/2011 | Derchak | G16H 20/30 |
| | | | | 600/301 |
| 2012/0150022 | A1* | 6/2012 | Bar-Tal | A61B 5/063 |
| | | | | 600/424 |
| 2014/0221803 | A1* | 8/2014 | Bar-Tal | A61B 5/063 |
| | | | | 600/373 |
| 2015/0141798 | A1* | 5/2015 | Bar-Tal | A61B 5/6852 |
| | | | | 600/409 |

FOREIGN PATENT DOCUMENTS

| | | | |
|---|---|---|---|
| EP | 2868272 | A1 | 5/2015 |
| EP | 3181046 | | 6/2017 |

\* cited by examiner

EXTENDING THE TRACKING VOLUME IN A PROBE TRACKING SYSTEM

CROSS-REFERENCE TO RELATED APPLICATIONS

This patent application claims the benefit of U.S. Provisional Application No. 62/740,012 filed Oct. 2, 2018.

FIELD OF THE INVENTION

The present invention relates generally to invasive medical procedures, and specifically to navigation of a probe used in such procedures.

BACKGROUND

U.S. Pat. No. 8,456,182 to Bar-Tal et al., whose disclosure is incorporated herein by reference, describes a method that includes positioning body-electrodes in galvanic contact with a body of a patient and positioning a mapping-tool, having a mapping-electrode, in a plurality of regions in the body. The method further includes tracking the mapping-tool at different positions in each of the regions using a location-measuring system, and for each region, generating a respective set of calibration-currents between the body-electrodes and the mapping-electrode at the different positions in the region. A respective relation is derived for each region between the respective set of the calibration-currents and the different positions and is used in determining the location of an investigation-tool in response to the different respective relations and investigation-tool-currents.

SUMMARY OF THE INVENTION

There is provided, in accordance with some embodiments of the present invention, a system including multiple electrically-conductive channels and a processor. The processor is configured to receive, over the electrically-conductive channels, (i) respective first electric currents from a probe, which is within a body of a patient, via a plurality of first electrodes, which are attached to skin of the patient at a region of the body, and (ii) a second electric current from the probe via a second electrode, which is attached to the skin and is connected to one of the channels. The processor is further configured to ascertain respective first electric-current values of the first electric currents and a second electric-current value of the second electric current, and to calculate a position of the probe between the region and the second electrode, based on the first electric-current values and the second electric-current value.

In some embodiments,
the region includes at least part of a thorax of the patient,
the first electrodes are attached to the thorax, and
the second electrode is attached to a thigh of the patient.

In some embodiments, the processor is configured to calculate the position of the probe by:
calculating a normalized current-value $I_N = I_2/I_T$, $I_2$ being the second electric-current value and $I_T$ being a sum of the first electric-current values and the second electric-current value, and
calculating the position of the probe by applying a linear function to $I_N$.

In some embodiments, the processor is further configured to learn the linear function prior to applying the linear function, based on a plurality of initial electric currents received from the probe via the first electrodes and the second electrode.

In some embodiments, the processor is further configured to:
ascertain that the position of the probe is within the first region, and
in response to the ascertaining, disconnect the second electrode from the one of the channels.

In some embodiments, the processor is further configured to calculate a deflection angle of the probe, based on the first electric-current values and the second electric-current value.

There is further provided, in accordance with some embodiments of the present invention, a system including a plurality of first electrodes, configured to, while attached to skin of a patient at a region of a body of the patient and connected to different respective electrically-conductive channels, receive respective first electric currents from a probe disposed within the body, such that the first electric currents are passed over the channels. The system further includes a second electrode, configured to, while attached to the skin, receive a second electric current from the probe. The system further includes a switch, configured to connect the second electrode to a particular one of the channels, while the probe is between the region and the second electrode, such that the second electric current is passed over the particular one of the channels.

In some embodiments, the switch is configured to connect the second electrode to the particular one of the channels by short-circuiting the second electrode to a particular one of the first electrodes.

In some embodiments, the switch is further configured to connect the second electrode to an ablation-signal generator, instead of to the particular one of the channels, while the probe is in the region.

In some embodiments,
the switch is a first switch, and
the system further includes a second switch configured to connect the second electrode to an ablation-signal generator while the probe is in the region and the second electrode is disconnected from the particular one of the channels.

In some embodiments,
the first switch is disposed internally to a console, and
the second switch is disposed internally to the ablation-signal generator.

There is further provided, in accordance with some embodiments of the present invention, a method including receiving, over multiple electrically-conductive channels, (i) respective first electric currents from a probe, which is within a body of a patient, via a plurality of first electrodes, which are attached to skin of the patient at a region of the body, and (ii) a second electric current from the probe via a second electrode, which is attached to the skin and is connected to one of the channels. The method further includes ascertaining respective first electric-current values of the first electric currents and a second electric-current value of the second electric current and calculating a position of the probe between the region and the second electrode, based on the first electric-current values and the second electric-current value.

There is further provided, in accordance with some embodiments of the present invention, a method including receiving, by a plurality of first electrodes attached to skin of a patient at a region of a body of the patient and connected to different respective electrically-conductive channels, respective first electric currents from a probe disposed within the body, such that the first electric currents are passed over the channels. The method further includes receiving, by a second electrode attached to the skin, a second electric current from the probe, and using a switch, connecting the second electrode to a particular one of the channels, while the probe is between the region and the second electrode, such that the second electric current is passed over the particular one of the channels.

In some embodiments,
the region includes at least part of a thorax of the patient,
the first electrodes are attached to the thorax, and
the second electrode is attached to a thigh of the patient.

There is further provided, in accordance with some embodiments of the present invention, a computer software product including a tangible non-transitory computer-readable medium in which program instructions are stored. The instructions, when read by a processor, cause the processor to receive, over multiple electrically-conductive channels, (i) respective first electric currents from a probe, which is within a body of a patient, via a plurality of first electrodes, which are attached to skin of the patient at a region of the body, and (ii) a second electric current from the probe via a second electrode, which is attached to the skin and is connected to one of the channels. The instructions further cause the processor to ascertain respective first electric-current values of the first electric currents and a second electric-current value of the second electric current, and to calculate a position of the probe between the region and the second electrode, based on the first electric-current values and the second electric-current value.

BRIEF DESCRIPTION OF THE DRAWINGS

The present invention will be more fully understood from the following detailed description of embodiments thereof, taken together with the drawings, in which.

DETAILED DESCRIPTION OF EMBODIMENTS

Overview

Figure 1:
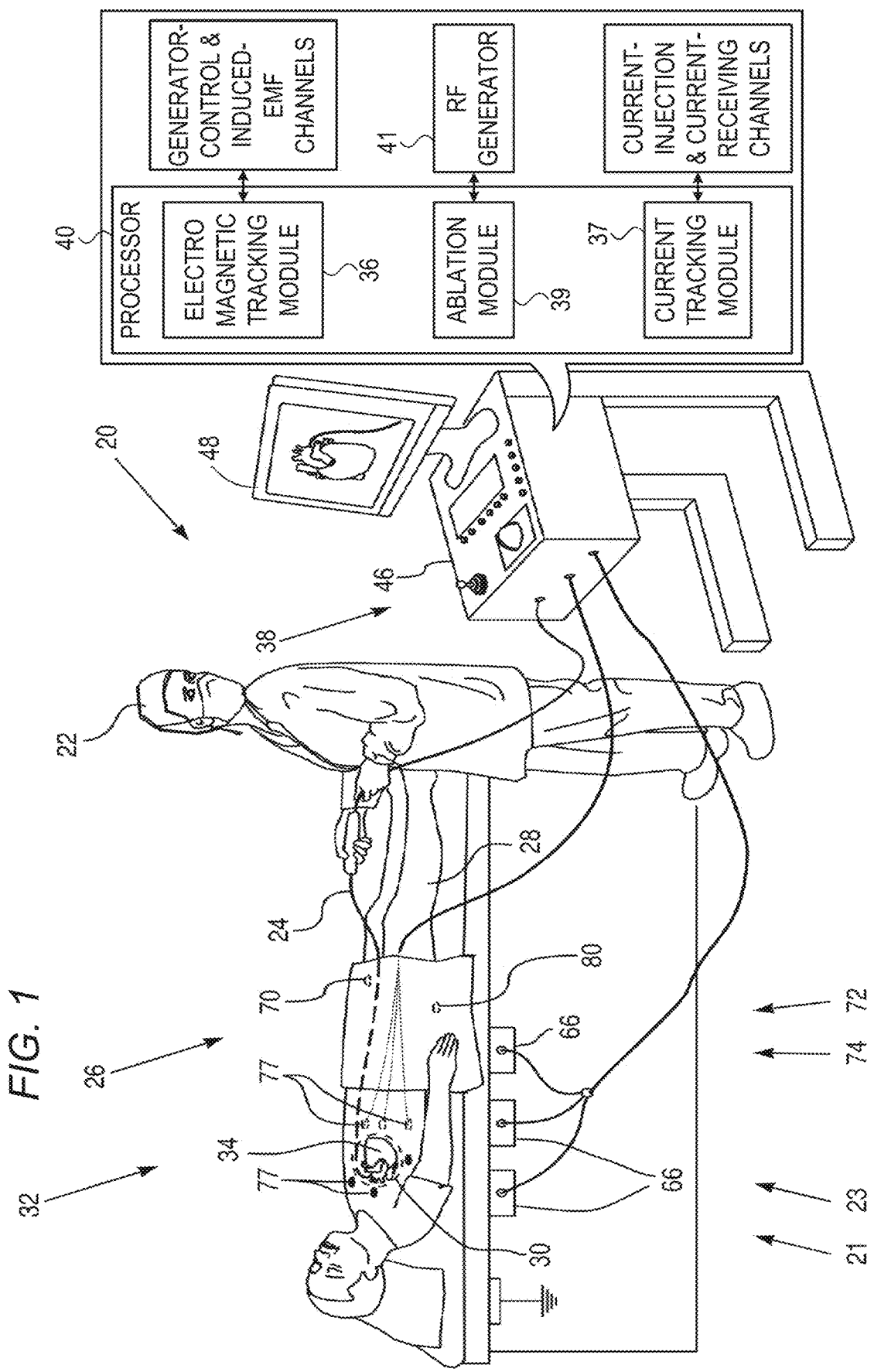
FIG. 1 is a schematic illustration of a probe tracking system, according to an embodiment of the present invention.

During some invasive cardiac procedures, a probe is inserted into the body of a patient, e.g., via a left or right femoral vein of the patient and is then advanced to the heart. Upon reaching the heart, the probe may be used for mapping and/or ablation.

In general, the probe may be well-tracked in the vicinity of the heart using one or more known tracking systems, e.g., a magnetic tracking system and/or an advanced current location (ACL) system. However, these systems are typically configured to track a probe only in a localized region, such as a volume containing the heart, and generally do not provide good, or even any, tracking outside the localized region. This may be problematic during the advancement of the probe to the heart, when the probe is relatively far from the heart. Alternative tracking solutions include fluoroscopy and ultrasound; however, fluoroscopy uses ionizing radiation, and ultrasound probes have limited capability.

To address this challenge, embodiments of the present invention augment an ACL system with an additional mapping electrode, which is coupled to the patient's body near the insertion point of the probe. The current received by the additional mapping electrode is used to track the probe while the probe is advanced to the heart. Embodiments of the present invention may be used with any probe comprising at least two electrodes separated by known distances, i.e., at least two electrodes whose positions relative to each other are known.

More particularly, immediately following the insertion of the probe into the patient, currents are injected into the probe electrodes, and in response the additional mapping electrode receives currents from the probe electrodes. It has been determined that there is a linear relationship between the received currents and the positions of the probe electrodes along an axis running from the entry point of the probe to the heart. Thus, provided that the relative electrode positions are known, the received currents may be used to learn the linear relationship. Subsequently to learning the linear relationship, the linear relationship is used to track the probe, in the one dimension referred to above, using the currents received by the additional mapping electrode as the probe is advanced through the vasculature of the patient.

System Description

In the following description, like elements in the drawings are identified by like numerals, and like elements are differentiated as necessary by appending a letter to the identifying numeral.

Figure 2:
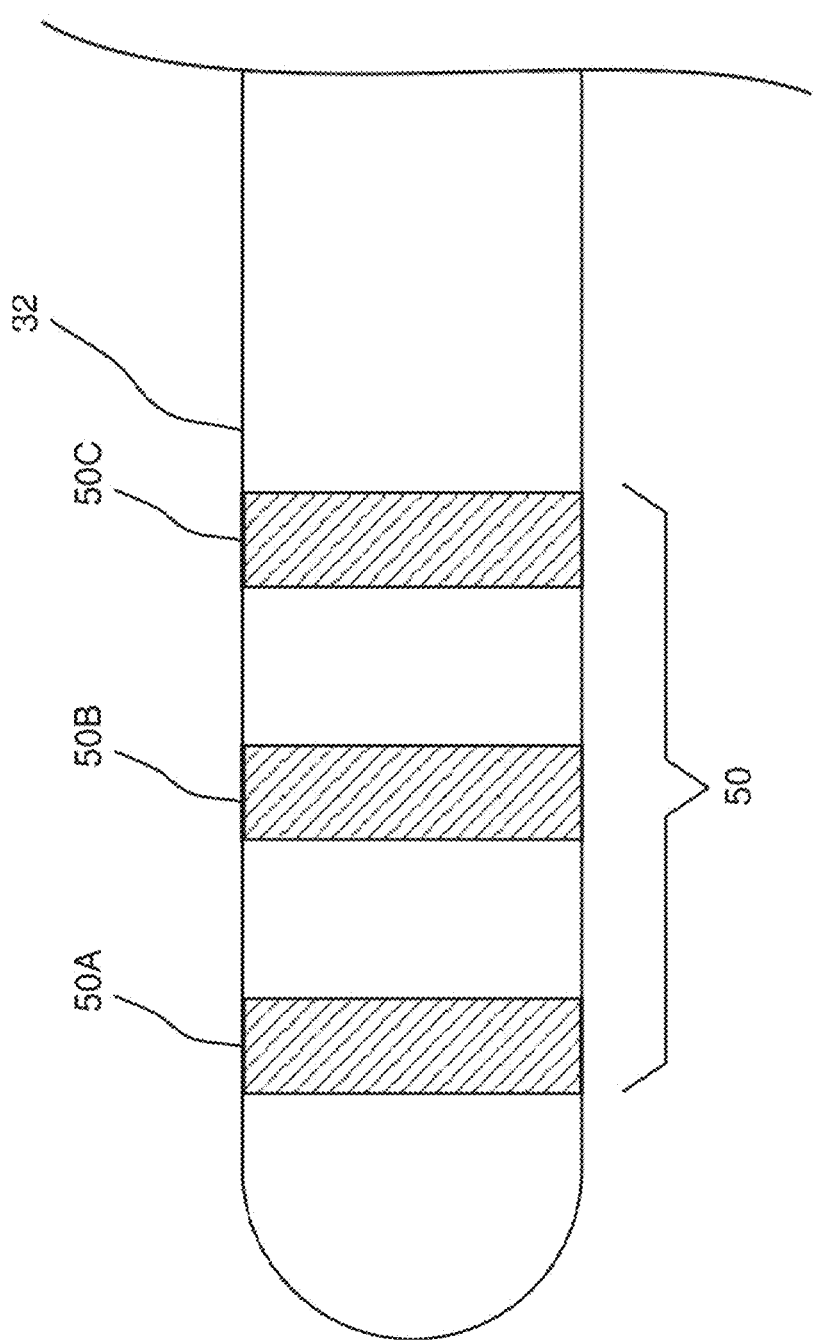
FIG. 2 is a schematic illustration of a distal portion of a probe tracked by the system, according to an embodiment of the present invention.

Reference is now made to FIG. 1, which is a schematic illustration of a probe tracking system 20, and to FIG. 2, which is a schematic illustration of a probe 32 tracked by the system, according to an embodiment of the present invention. In some embodiments, probe 32 is a distal portion of a catheter 24.

For simplicity and clarity, the following description, except where otherwise stated, assumes a medical procedure is performed by an operator 22 of system 20, herein assumed to be a medical practitioner, wherein the operator inserts catheter 24 into a left or right femoral vein 26 of a patient 28. The procedure may comprise, for example, investigation and/or ablation of a heart 34 of the patient. Typically in the procedure, the catheter is initially inserted into the patient until probe 32 reaches a desired location in, or in proximity to, heart 34 of the patient.

During the procedure, a plurality of patch electrodes 77, also referred to herein as "skin patches," "patches," "skin electrodes," or "electrodes," are attached to the skin of patient 28 at a particular region of the patient's body referred to herein as a mapping region 30. Typically, mapping region 30 includes at least part of the patient's thorax, such as at least part of the patient's heart, and electrodes 77 are attached to skin of the thorax, such as the skin of the chest and/or the back of the patient. By way of example, the present description assumes six patches 77 attached to the skin of patient 28 near the patient's heart.

System 20 comprises a processor 40, which performs the functionality described herein by executing various modules, each of which may comprise any suitable hardware and/or software elements. The modules include a current tracking module 37, and may include, in addition, an electromagnetic tracking module 36 and/or an ablation module 39. The functions of the modules are described in more detail below. In general, the function of a particular module may be said to be performed by the module, or by the processor by executing the module.

Processor 40 is typically mounted in a console 46, which comprises operating controls 38, typically including a pointing device such as a mouse or trackball, that operator 22 uses to interact with the processor. Results of the operations performed by processor 40 are presented to the operator on a display 48, which typically presents a visual representation of the path taken by probe 32 in patient 28.

In general, processor 40 may be embodied as a single processor, or as a cooperatively networked or clustered set of processors. In some embodiments, the functionality of processor 40, as described herein, is implemented solely in hardware, e.g., using one or more Application-Specific Integrated Circuits (ASICs) or Field-Programmable Gate Arrays (FPGAs). In other embodiments, the functionality of processor 40 is implemented at least partly in software. For example, in some embodiments, processor 40 is embodied as a programmed digital computing device comprising at least a central processing unit (CPU) and random-access memory (RAM). Program code, including software programs, and/or data are loaded into the RAM for execution and processing by the CPU. The program code and/or data may be downloaded to the processor in electronic form, over a network, for example. Alternatively or additionally, the program code and/or data may be provided and/or stored on non-transitory tangible media, such as magnetic, optical, or electronic memory. Such program code and/or data, when provided to the processor, produce a machine or special-purpose computer, configured to perform the tasks described herein.

For tracking the path of probe 32 in mapping region 30, which contains heart 34, embodiments of the present invention use a first, current based, tracking system 21, and may also use a second, electromagnetic based, tracking system 23. Both systems are described below, and, as is also described in more detail below, in embodiments of the present invention the first tracking system is modified to enable tracking of probe 32 outside region 30.

First tracking system 21 comprises a current measuring tracking system, similar to that described in U.S. Pat. No. 8,456,182 to Bar-Tal et al., whose disclosure is incorporated herein by reference. (An example of such a system is an ACL system.) The Carto™ system produced by Biosense-Webster of 33 Technology Drive, Irvine, Calif. 92618 USA, also uses a current measuring tracking system. The current measuring tracking system is under control of current tracking module 37. Probe has one or more probe electrodes 50A, 50B, 50C, . . . , generically termed probe electrodes 50 as illustrated in FIG. 2. In first tracking system 21, module 37 injects currents to selected electrodes 50 being tracked. The currents are received by patch electrodes 77 and are transferred to current tracking module 37 over different respective electrically-conductive channels. Thus, first tracking system 21 comprises electrodes and module 37. (Although conductive cabling for patch electrodes 77 and for other skin electrodes described herein is present for each of the electrodes, for clarity cabling is only shown in the figure for some of the electrodes.)

The currents between a given probe electrode 50 and skin patches 77 vary according to the location of the probe electrode, because, inter alia, of the dependency of the impedance between the electrode and each patch on the distance of the electrode from the patch. Module 37 measures the respective currents received by patches 77. In response thereto, module 37 calculates the position of each probe electrode, and hence, the position of the probe, as further described below. In response to calculating the position of the probe, module 37 may generate an indication (e.g., a visual indication on display 48) of the position of the probe.

As noted above, skin patches 77 are located at mapping region 30, so that module 37 is able to determine the location of a given electrode 50 within mapping region 30, from the different patch currents, when the electrode is present in the region.

In addition to skin patches 77, embodiments of the present invention utilize another mapping electrode, referred to herein as an "additional mapping electrode." In some embodiments, the additional mapping electrode is an extra skin patch 70 that is attached to the skin of patient 28, typically such that the insertion point of the probe is between patch 70 and electrodes 77. For example, patch 70 may be attached to the skin of the patient's thigh below (i.e., inferiorly to) the point at which the probe is inserted into the patient's femoral vein. Alternatively, for cases in which the probe is inserted into a cephalic vein or another vein in the patient's arm, the patch may be attached to the skin of the arm distally to the insertion point, i.e., between the insertion point and the patient's hand. (In some embodiments, a distance of at least 30 cm separates patch 70 from the nearest electrode 77.) Similarly to electrodes 77, extra skin patch 70 is configured to receive electric currents from the probe while attached to the skin. The manner in which these currents are used by first tracking system 21 is described below.

When implemented, second tracking system 23 comprises an electromagnetic tracking system, similar to that described in U.S. Pat. No. 6,690,963 to Ben-Haim et al., whose disclosure is incorporated herein by reference, and to that used in the Carto™ system produced by Biosense-Webster. The electromagnetic tracking system is under control of electromagnetic tracking module 36. The electromagnetic tracking system comprises a plurality of magnetic field generators, herein assumed to comprise three sets of generators 66, each set comprising three orthogonal coils, so that the plurality of generators comprises a total of nine coils. Generators 66 are placed in known locations beneath patient 28, the known locations defining a frame of reference of the generators. Module 36 controls, inter alia, the amplitude and frequency of the alternating magnetic fields produced by the generators.

The alternating magnetic fields interact with a coil located in probe 32, so as to generate an alternating electromotive force (EMF) in the coil, and the EMF is received as a signal by tracking module 36. The module analyzes the received signal, and from the analysis is able to determine a location and an orientation of the probe coil in the defined frame of reference.

Typically, the tracking by the first tracking system, or by both of the tracking systems, is presented visually on display 48, for example by incorporating an icon representing the probe into an image of patient 28, as well as, optionally, a representation of the path taken by the probe.

Figure 3:
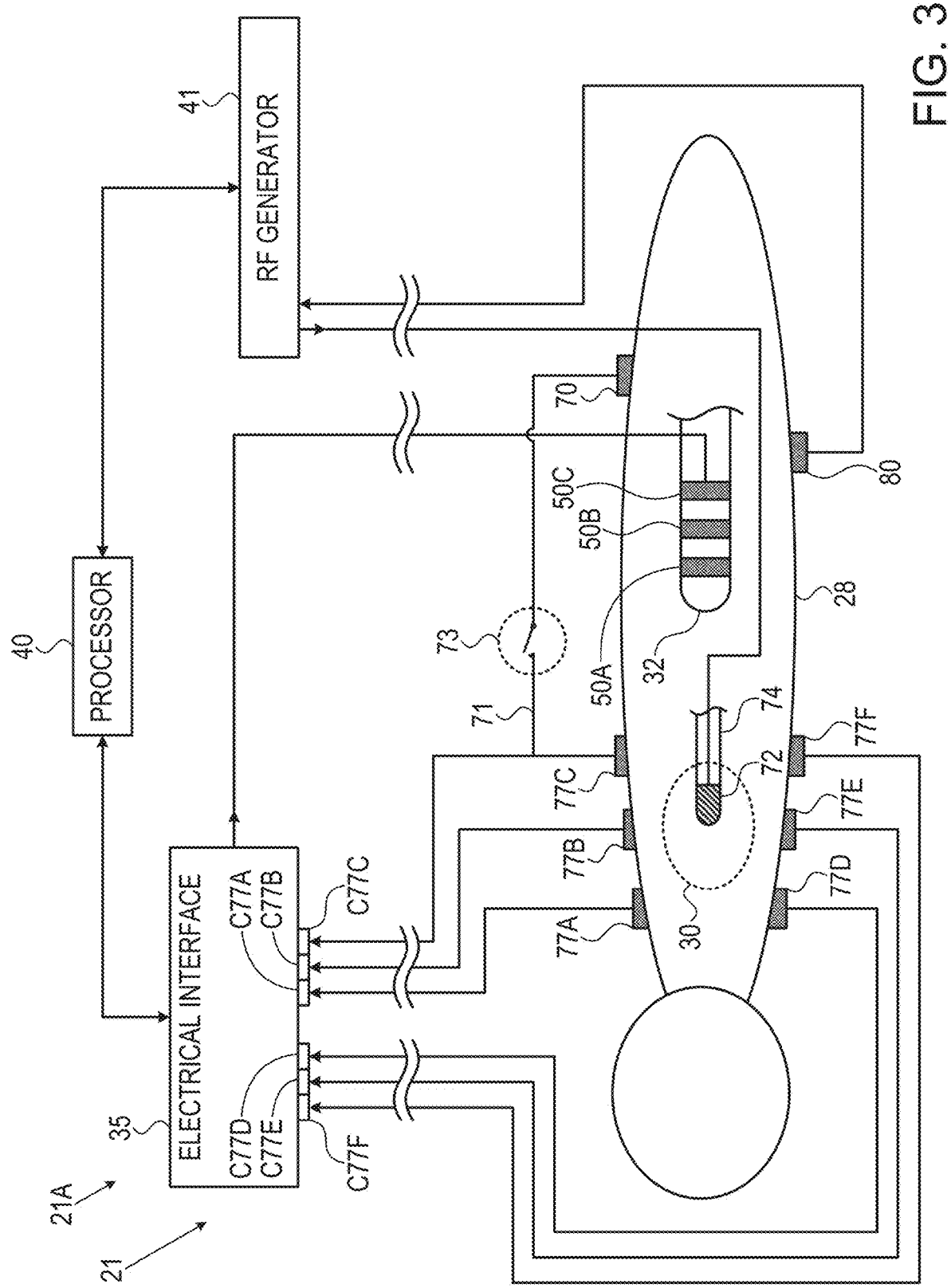
FIG. 3 is a schematic diagram illustrating electrical connections for a first modification of a tracking system, according to an embodiment of the present invention.
Figure 4:
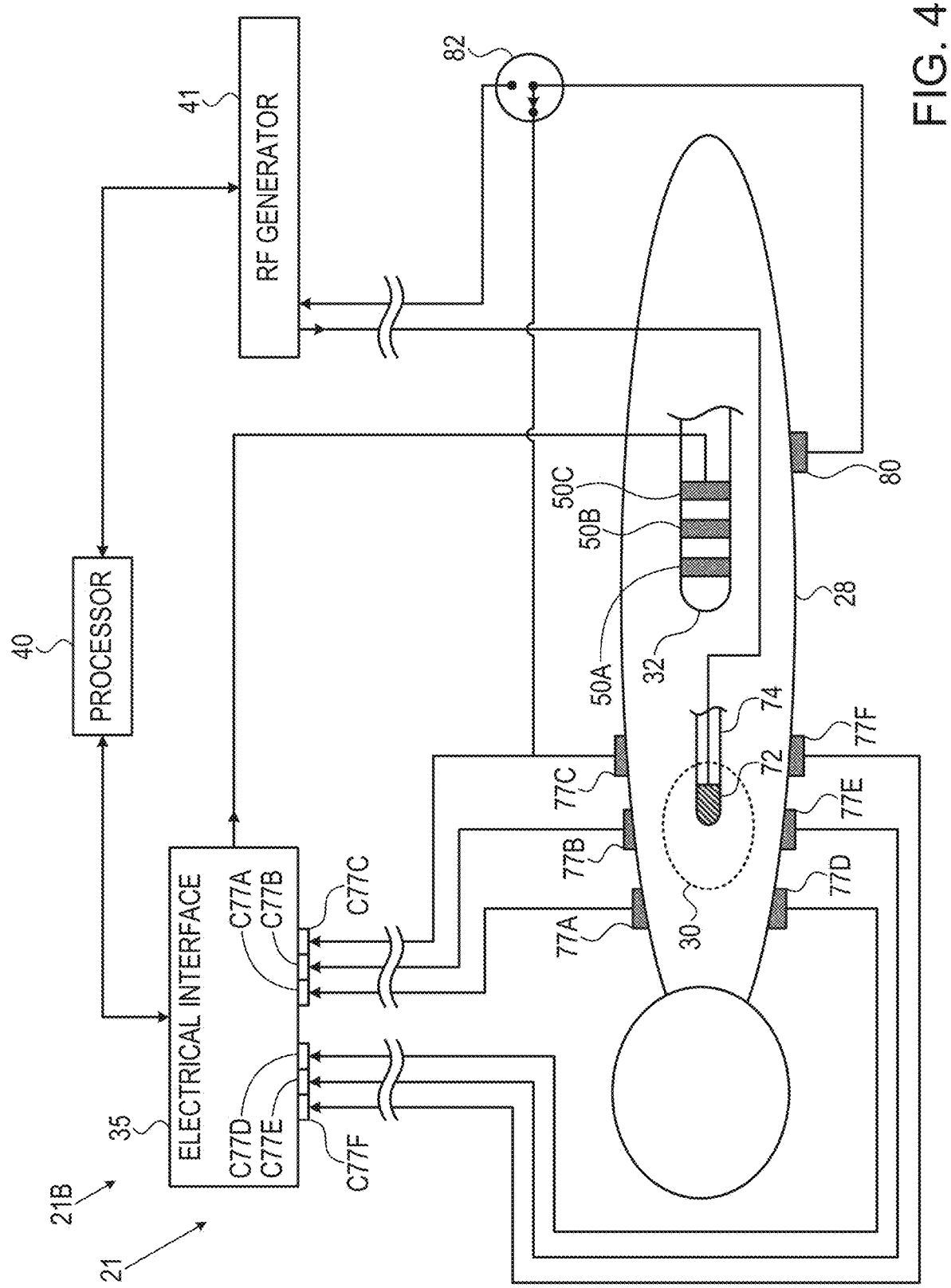
FIG. 4 is a schematic diagram illustrating electrical connections for a second modification of the tracking system, according to an embodiment of the present invention.
Figure 5:
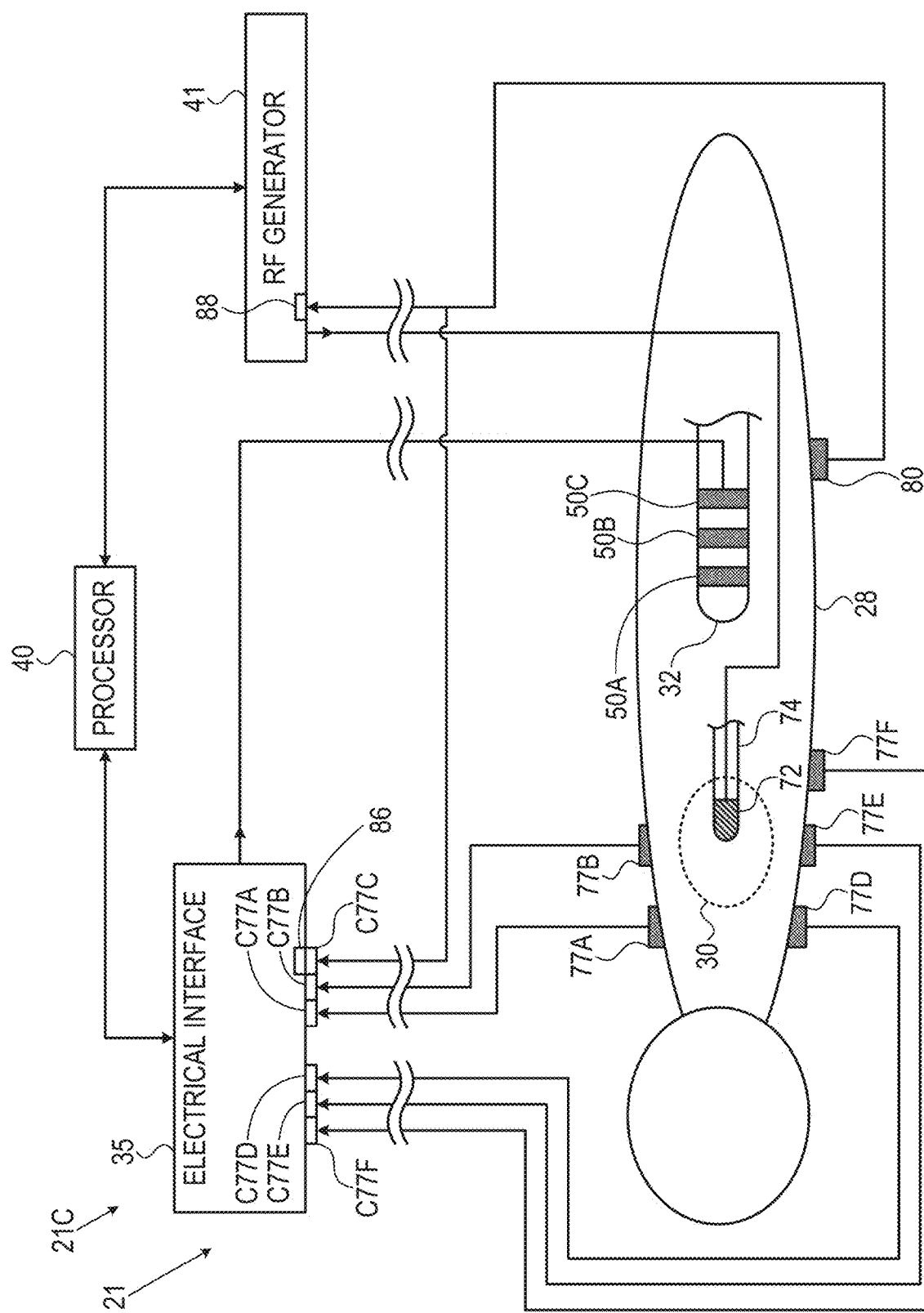
FIG. 5 is a schematic diagram illustrating electrical connections for a third modification of the tracking system, according to an embodiment of the present invention.

Ablation module 39 communicates with a radiofrequency (RF) generator 41, which delivers RF power to a region of heart 34 that is selected by operator 22. Operator 22 selects the region by positioning an ablation probe, with an ablation electrode, at the region. While probe 32 and one of electrodes 50 may be used as an ablation probe and an ablation electrode, for clarity the description herein assumes use of a separate ablation probe 74 having an ablation electrode 72. (FIGS. 3, 4, and 5 illustrate probe 74 and electrode 72.)

The level of RF power, and the time period during which the RF power is delivered, may be set by operator 22 using controls 38. The current from the RF power delivered by generator 41 to the patient through ablation electrode 72 returns to the generator via a return electrode 80, also herein termed an RF indifferent electrode. Return electrode 80 is attached to the skin of patient 28, typically to skin of the patient's lower back. In some embodiments, as further described below, return electrode 80 is used as an additional mapping electrode, alternatively to extra patch 70.

Current tracking module 37 communicates with the respective channels over which current is injected into electrodes 50, along with the respective channels over which current is received from the patch electrodes, as further described below with reference to FIG. 3. Electromagnetic tracking module 36 communicates with the channels over which generator-control signals are sent to generators 66, along with the channels over which induced EMFs are received from the coil in probe 32.

As stated above, embodiments of the invention modify the first tracking system to enable tracking of probe 32 outside region 30. Each of the modifications described hereinbelow connects the additional mapping electrode to a particular one of the channels over which the patch currents are received, while the probe is between mapping region 30 and the additional mapping electrode. Based on the electric currents passed via the additional mapping electrode over the particular one of the channels, processor 40 calculates the position of the probe.

First Modification

FIG. 3 is a schematic diagram illustrating electrical connections for a first modification 21A of first tracking system 21, according to an embodiment of the present invention. In the figure, patient 28 is shown schematically as a circle and an ellipse, and patch electrodes 77, attached to the patient, have been identified as three patches 77A, 77B, 77C on the front of the patient, and three patches 77D, 77E, and 77F on the patient's back.

Each patch 77 is connected to a different respective electrically-conductive channel, such that each patch passes its received electric currents over a different respective one of the channels. By way of example, FIG. 3 shows six channels C77A, C77B, C77C, C77D, C77E, and C77F, generically termed channels C77. (Electrode 77A is connected to channel C77A, electrode 77B to channel C77B, etc.) Each channel may comprise any suitable electrically-conducting elements such as one or more wires (or "lines"), ports, or sockets. Each channel may be located externally and/or internally to console 46 (FIG. 1). By way of example, the figures herein assume that channels C77 belong to an electrical interface 35 in console 46.

While probe 32 and ablation probe 74 are not drawn to scale, FIG. 3 assumes that ablation electrode 72 is within region 30, and that probe 32 is outside the region. However, system 21 and its modification do not depend on the presence and functioning of probe 74.

In the first modification, system 21 is modified by attaching extra patch electrode 70 to the skin of patient 28. The extra patch is typically attached to the patient at a point on the patient close to an expected path between an insertion point of catheter 24 into patient 28 and region 30, and typically below the insertion point. Thus, if the insertion point is the left or the right femoral vein, and the probe path is expected to continue along either of these veins, extra patch 70 may be attached to the lower thigh of the patient.

Extra patch 70 is galvanically connected to one of channels C77 by an electrically conducting line 71. For example, line 71 may connect patch 70 to one of the channels in lieu of one of patch electrodes 77 of system 21. Alternatively, as shown in FIG. 3, line 71 may galvanically connect (or "short-circuit") patch 70 to one of patch electrodes 77 of system 21, herein by way of example assumed to be electrode 77C.

In some embodiments, line 71 includes a switch 73, which is configured to be closed, and hence maintain the connection of electrode 70, at least while the probe is between mapping region 30 and electrode 70. When provided, switch 73 may be opened and closed by processor 40, or by operator 22, as described below. For clarity, except where stated otherwise, in the following description switch 73 is assumed to be absent.

It will be understood that first modification 21A comprises electrodes 77 and extra patch electrode 70 connected as described above. First modification 21A is able to track any of electrodes 50 on probe 32, but for simplicity, except where stated below, the description assumes that only electrode 50C is tracked.

The addition of extra patch electrode 70 creates a "split patch" providing a single current, from the current injected into electrode 50C, to channel C77C. The single current is derived from patches 70 and 77C, and depends, inter alia, on the positioning of electrode 50C with respect to the two patches. Hence, measuring this current provides an indication of the position of electrode 50C outside region 30, as described in detail below.

An advantage of first modification 21A is that the additional tracking functionality provided by electrode 70 does not require the addition of an electrically-conductive channel; rather, electrode 70 is simply connected to an existing channel.

Second Modification

FIG. 4 is a schematic diagram illustrating electrical connections for a second modification 21B of first tracking system 21, according to an embodiment of the present invention. Apart from the differences described below, the operation of modification 21B is generally similar to that of modification 21A (FIG. 3) and elements indicated by the same reference numerals in both modifications are generally similar in construction and in operation.

In contrast to modification 21A, there is no extra patch electrode 70 in modification 21B. Rather, in modification 21B, return electrode 80 functions as the additional mapping electrode, by virtue of being connected to one of the channels when the return electrode is not connected to RF generator 41. For example, a switch 82, in a first configuration, may galvanically connect indifferent electrode 80 to one of the channels, e.g., by short-circuiting electrode 80 to one of electrodes 77, herein assumed to be electrode 77C, such that the indifferent electrode is disconnected from the return of RF generator 41. The first configuration is illustrated in FIG. 4.

In the first configuration, since the return of RF generator 41 is disconnected from the indifferent electrode, the RF generator is inoperative, and no ablation current is transferred from ablation electrode 72. In addition, the connected indifferent electrode and patch 77C act as a split patch, providing a single current, from the current injected into electrode 50C, to channel C77C. As for the first embodiment, the single current depends, inter alia, on the positioning of electrode 50C with respect to indifferent electrode 80 and patch 77C, and measuring this current provides an indication of the position of electrode 50C outside region 30.

In a second configuration of switch 82, the switch connects indifferent electrode 80 to the return of RF generator 41, such that the indifferent electrode is disconnected from channel C77C. In this configuration, RF generator 41 is operative, and is able to deliver ablation current to electrode 72.

In general, switch 82 is in the first configuration when the probe is between mapping region 30 and return electrode 80, and is in the second configuration when the probe is in the mapping region. Switch 82 may be operated manually or by processor 40.

An advantage of second modification 21B is that no extra electrode is required. Moreover, as in the case of first modification 21A, no additional electrically-conductive channels, or changes to the RF generator, are required.

Third Modification

FIG. 5 is a schematic diagram illustrating electrical connections for a third modification 21C of first tracking system 21, according to an embodiment of the present invention. Apart from the differences described below, the operation of modification 21C is generally similar to that of modifications 21A and 21B (FIGS. 3 and 4) and elements indicated by the same reference numerals in the three modifications are generally similar in construction and in operation.

Third modification 21C is similar to second modification 21B, in that additional tracking functionality is provided by return electrode 80. However, instead of a single switch controlling the galvanic connection of return electrode 80, two switches control this connection: a first switch 86 controls the connection to the channel, while a second switch 88 controls the connection to the RF generator.

In some embodiments, as shown in FIG. 5, first switch 86 is disposed internally to electrical interface 35 of the console, and second switch 88, which may be referred to as an "idling switch," is disposed internally to RF generator 41. Hence, given that RF generator 41 is typically internal to the console, both of the switches may be internal to the console. In such embodiments, return electrode 80 is not connected to patch 77C, and the switches are controlled by processor 40.

There are two states of operation of third modification 21C. In a first state, second switch 88 is open, so that the RF generator does not provide any ablation power and so that its return line is isolated from indifferent electrode 80. Also in the first state, first switch 86 is closed so that there is a galvanic connection between the indifferent electrode and channel C77C. In this first state, indifferent electrode 80 effectively replaces patch 77C, and because of the position of the indifferent electrode, tracking of electrodes 50 may be implemented between the indifferent electrode and region 30.

In a second state of operation of third modification 21C, idling switch 88 is closed, so that ablation power may be provided to electrode 72. Also in the second state, first switch 86 is open so that there is no galvanic connection between the indifferent electrode and channel C77C. In the second state, tracking of electrodes 50 in region 30 may be implemented, based on the currents received from the five connected patches 77A, 77B, 77D, 77E, and 77F.

As in the case of second modification 21B, third modification 21C does not require any extra electrode. Moreover, the provision of internal switches, rather than external switches, may simplify use of the system by the operator.

Introduction to Tracking Techniques

As described above, while the probe is between mapping region 30 and the additional mapping electrode, a plurality of electric currents, including an electric current from the additional mapping electrode, are received over channels C77. After passing over the channels, the currents pass through analog-to-digital (A/D) conversion circuitry, which is typically located within console 46 (FIG. 1). The currents may further pass through denoising circuitry, and/or any other suitable circuitry. The digitized signals are received by current tracking module 37 (FIG. 1), which is executed by processor 40. In view of the above, it is noted that in the context of the present application, including the claims, the processor may be said to receive a signal via one of the patches even though the processor does not receive the signal in its raw form.

For each received current, current tracking module 37 ascertains (or "measures") the value of the current. As described in detail below, based on the electric-current values, the current tracking module calculates the position of the probe between the mapping region and the additional mapping electrode. In some embodiments, the processor also calculates a deflection angle of the probe, based on the electric-current values.

Typically, the position of the probe is calculated in one dimension, along an axis running between the mapping region and the region of the additional mapping electrode. For example, for embodiments in which the mapping region is in the patient's thorax and the additional mapping electrode is attached to the patient's thigh, the processor may calculate the position of probe along the patient's superior-inferior axis.

Notwithstanding the above, in some embodiments, the position of the probe is calculated in more than one dimension, based on electric-current values from multiple additional mapping electrodes. For example, two extra skin patches 70 may be coupled to the patient's skin inferiorly to the insertion point, one on the patient's right thigh and the other on the patient's left thigh. Subsequently, based on the signals from the two extra skin patches, the position of the probe may be calculated along the patient's superior-inferior axis and also along the patient's lateral-medial axis. The second extra skin patch may be galvanically connected to another one of patches 77 (such as patch 77B) per first modification 21A, or to an extra, dedicated channel C77.

As further described below, the processor typically calculates the position of each probe electrode by (i) calculating a normalized current-value $I_N = I_2/I_T$, where, for the current injected into the probe electrode, $I_2$ is the value of the current from the additional mapping electrode and $I_T$ (or "$I_{total}$") is sum of the values of the currents, and (ii) applying a linear function to $I_N$. The position of any of the probe electrodes may then be taken as the position of the probe; alternatively, the position of the probe may be defined as the average of the respective probe-electrode positions.

By tracking the position of the probe, the processor may ascertain when the position of the probe is within mapping region 30. In response to ascertaining that the probe has reached the mapping region, the processor may disconnect the additional mapping electrode from channel C77C, e.g., by controlling switch 73 (FIG. 3) or switch 82 (FIG. 4), or switches 86 and 88 (FIG. 5).

Prior to applying the linear function, the processor typically learns the linear function, based on initial electric currents received from the probe via electrodes 77 and the additional mapping electrode.

Figure 6:
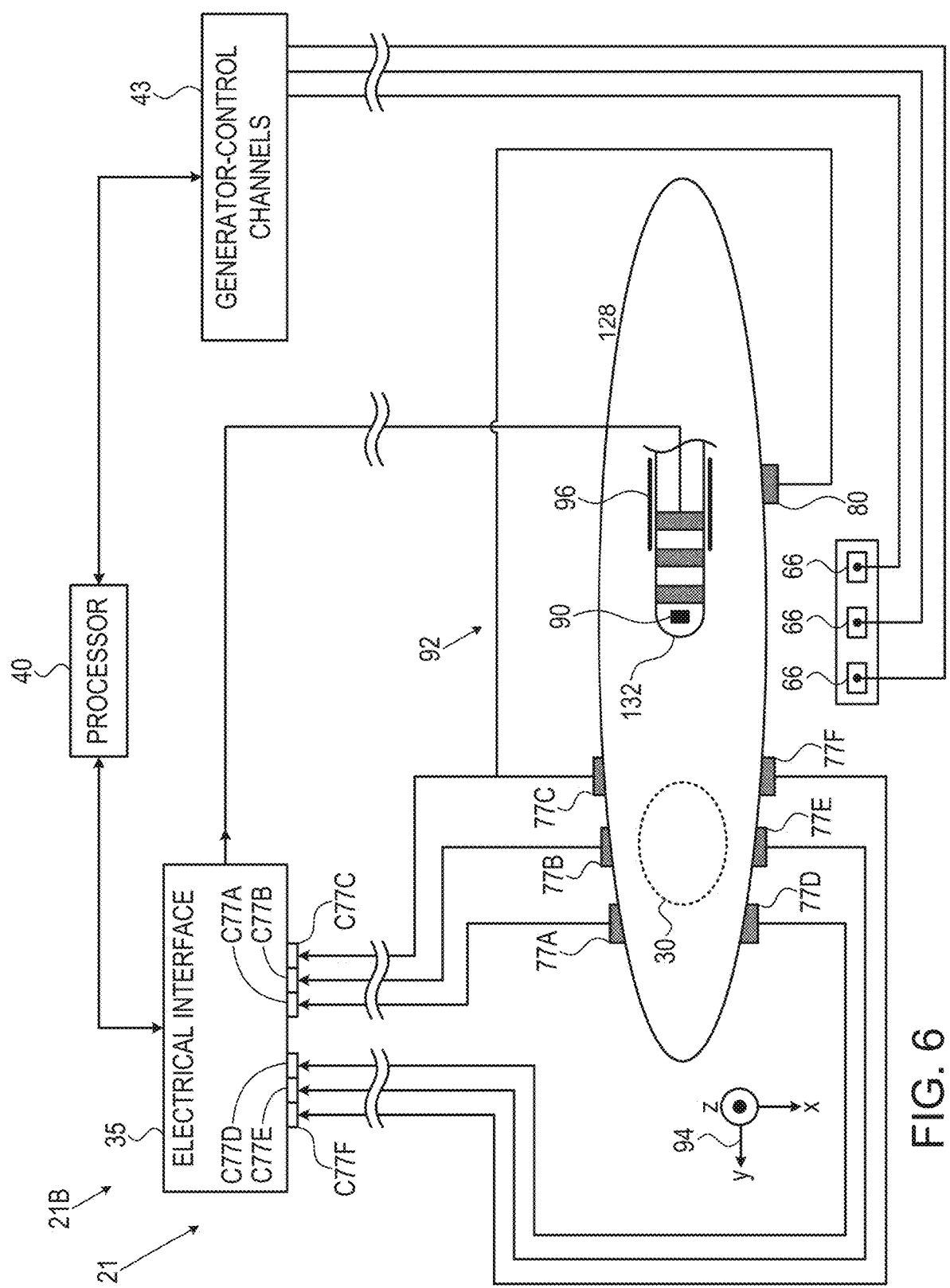
FIG. 6 is a schematic illustration of an experimental setup.
Figure 7:
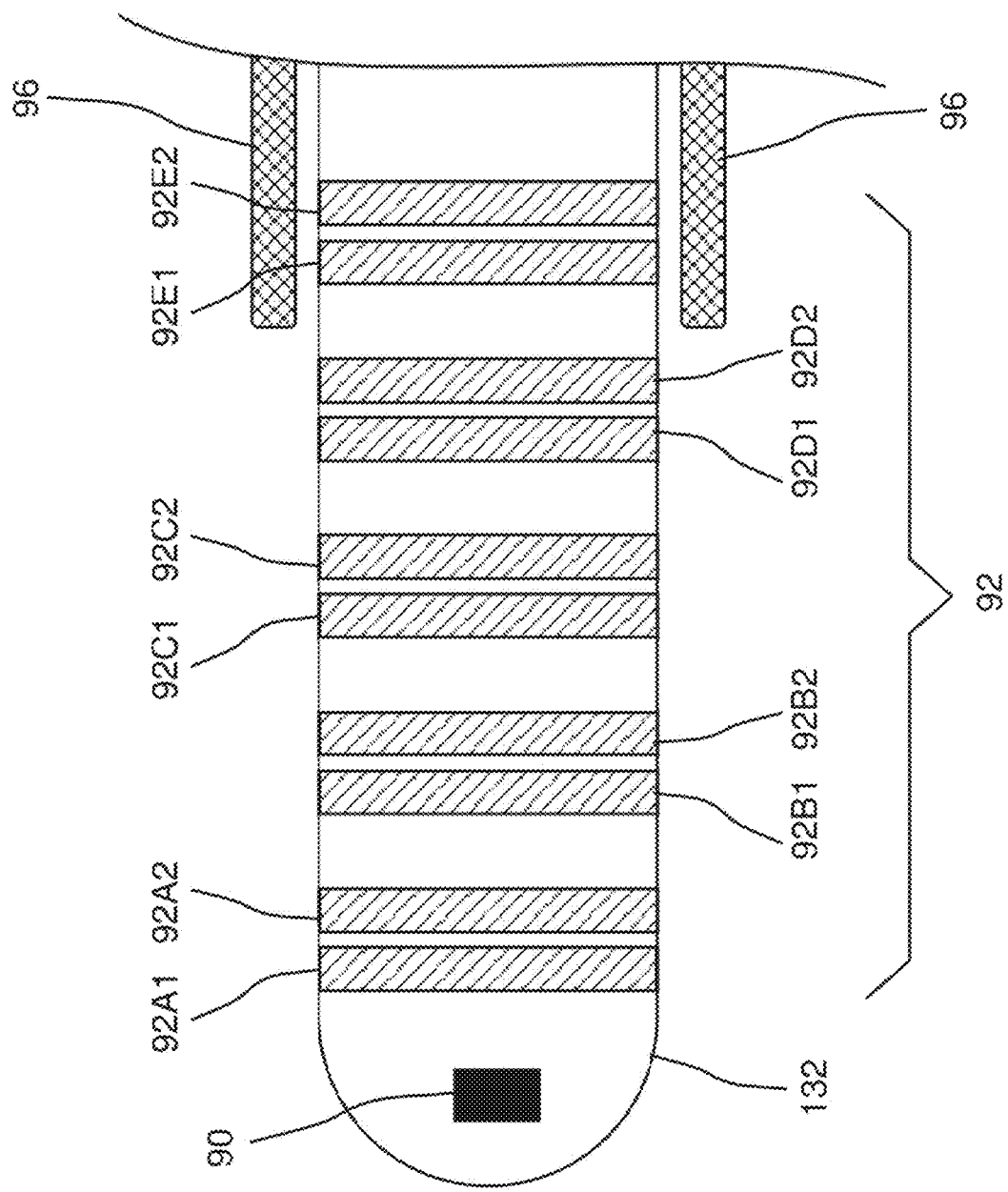
FIG. 7 is a schematic illustration of a distal probe used in the setup.
Figure 8:
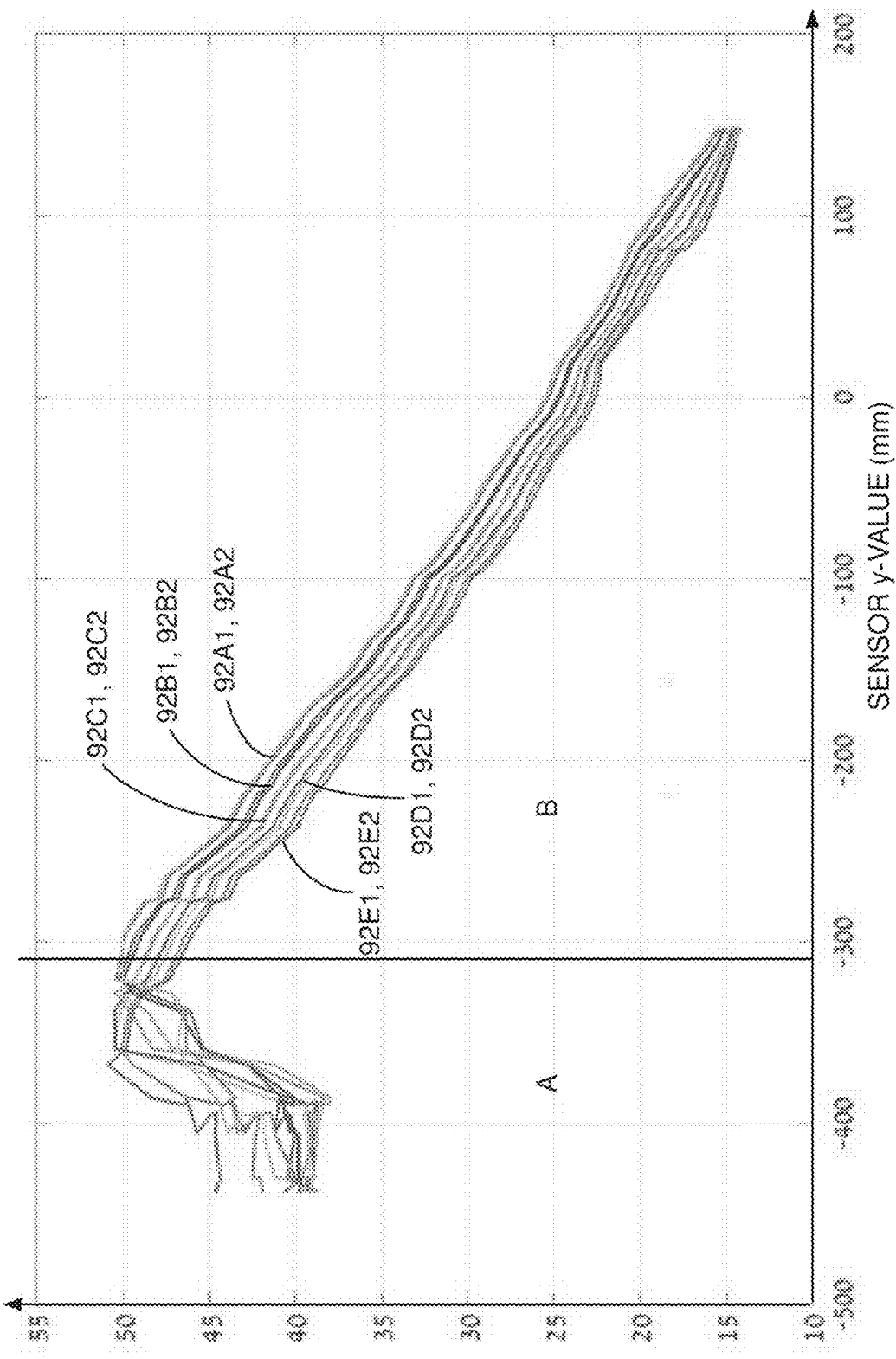
FIG. 8 is a schematic graph of results from the setup, according to an embodiment of the present invention.

To help explain the theoretical basis for the tracking techniques described herein, reference is now made to FIGS. 6-8. FIG. 6 is a schematic illustration of an experimental setup, FIG. 7 is a schematic illustration of a distal probe used in the setup, and FIG. 8 is a schematic graph of results from the setup, according to an embodiment of the present invention.

To validate the tracking performed by embodiments of the invention, the inventors applied elements of second modification 21B, in its first configuration, to a pig 128. Thus, six patches 77 were attached to the skin of the pig; in addition, indifferent electrode 80 was attached to the pig, and was galvanically connected to patch 77C. Except as otherwise stated, the experimental setup described herein assumes that a probe 132, which is the distal portion of a catheter generally similar to catheter 24, was inserted into the pig 128.

To track probe 132 in the pig, a triple axis coil sensor 90 was incorporated in a known position into the probe, and electromagnetic tracking system 23 was used to track the position of the sensor. As described above, system 23 uses magnetic generators 66 and electromagnetic tracking module 36 (FIG. 1), executed by processor 40, to induce a signal in sensor 90, to analyze the signal, and to find the position of the sensor from the analyzed signal. (The electromagnetic tracking module communicates control signals to the generators over generator-control channels 43.) The position was found in a frame of reference 94 defined by generators 66, the frame of reference having orthogonal axes where a positive y-axis is assumed to be parallel to, and in the same direction as, the longitudinal axis of the pig in the superior direction. (The longitudinal axis of the pig is analogous to the superior-inferior axis in a human patient.)

For the experimental setup, probe 132 was cylindrical, and comprised five pairs of bipolar electrodes 92, i.e., ten electrodes 92A1, 92A2, 92B1, 92B2, . . . 92E1, and 92E2, where electrode 92A1 is the most distal electrode, and electrode 92E2 is the most proximal. The positions and spacings of the electrodes along probe 132 were measured, and this spacing remained constant during the experiment.

Initially, an electrically-insulative sheath 96 was inserted several millimeters into a femoral vein of the pig. Probe 132 was inserted into the sheath, and current tracking module 37 (FIG. 1), executed by processor 40, injected respective currents into the ten electrodes 92 of the probe.

During the experiment, current tracking module 37 measured the current received by channel C77C, $I_{C77C}$, from patch 77C and indifferent electrode 80. From this measured current, the current received by indifferent electrode 80 was estimated, as explained below:

Module 37 measured the five currents from patches 77A, 77B, 77D, 77E, and 77F, received by their respective channels in the module, to find a total current for these patches. The module then added the current received by channel C77C to find a total current received by module 37, $I_{total}$. A normalized current to channel C77C was then calculated as the ratio $I_N$:

$$I_N = \frac{I_{C77C}}{I_{total}} \quad (1)$$

Typically, for a probe in region 30, the current in channel C77C (i.e., the current from patch 77C) is substantially equal to each of the currents from patches 77A, 77B, 77D, 77E, and 77F, and so $I_N$ is approximately ⅙, i.e., approximately 17%. Any value above this gives an estimate of the normalized current from the indifferent electrode.

FIG. 8 is a schematic graph of normalized current, $I_N$, for each of the ten electrodes 92 vs. the measured position of sensor 90, as probe 132 is moved though the femoral vein of pig 128. As stated above, the position of sensor 90 was measured using electromagnetic tracking module 36, and the position measured was the y-value of the sensor.

The graph is divided into two sections: a first region A, which corresponds to a state when all or some of electrodes 92 were within the sheath, and a second region B, which corresponds to a state when all of the electrodes had exited from the sheath.

The graph illustrates that as the probe approached the distal end of the sheath, the normalized currents from each electrode 92 increased to a maximum current, which is approximately 50%. On exit from the sheath, each normalized current decreased from the maximum current.

As is apparent from the graph, in region B the normalized currents from electrodes 92 decreased monotonically as the probe moved away from the additional mapping electrode. As is also apparent from the graph, the change of normalized current with respect to the measured y-value is linear.

Thus, each line of the graphs may be represented by an equation:

$$I_N = m \cdot y + b \quad (2)$$

where m is the slope of the $I_N$ vs. y graph, and b is the vertical axis intercept of the $I_N$ vs. y graph.

While the experiment described above was performed for a configuration based on the second modification described above, the inventors have verified that the linear change of current with respect to y-value holds for the other modifications described herein.

Tracking the Probe

The experiment described above demonstrates that the normalized current varies linearly with the position of the probe along the superior-inferior axis. As described below, processor 40 is configured to learn this linear relationship, even without using an electromagnetic tracking system, and to then use the learned linear relationship to track the probe.

By way of introduction, it is noted that equation (2) may be rewritten:

$$y = \frac{I_N - b}{m} \text{ or} \quad (3)$$

-continued $$y = M \cdot I_N + B$$

where M is a parameter of equation (3) corresponding to the slope of a y vs. $I_N$ graph, and B is a parameter of equation (3) corresponding to the vertical axis intercept of the y vs. $I_N$ graph.

Hence, as is explained below with reference to the flowchart of FIG. 9, processor 40 may formulate an equation, in the form of equation (3), to calculate values of y from measured values of $I_N$, for each of the electrodes on probe 32.

It is noted that equation (3) is a linear relationship between a y-position and a normalized current for each electrode. In the disclosure and in the claims, if a linear relationship exists between a first variable such as the y-position, and a second variable such as the normalized current, then there is a constant ratio between a change of the first variable and the corresponding change of the second variable. For example, equation (3) has a constant ratio M.

Figure 9:
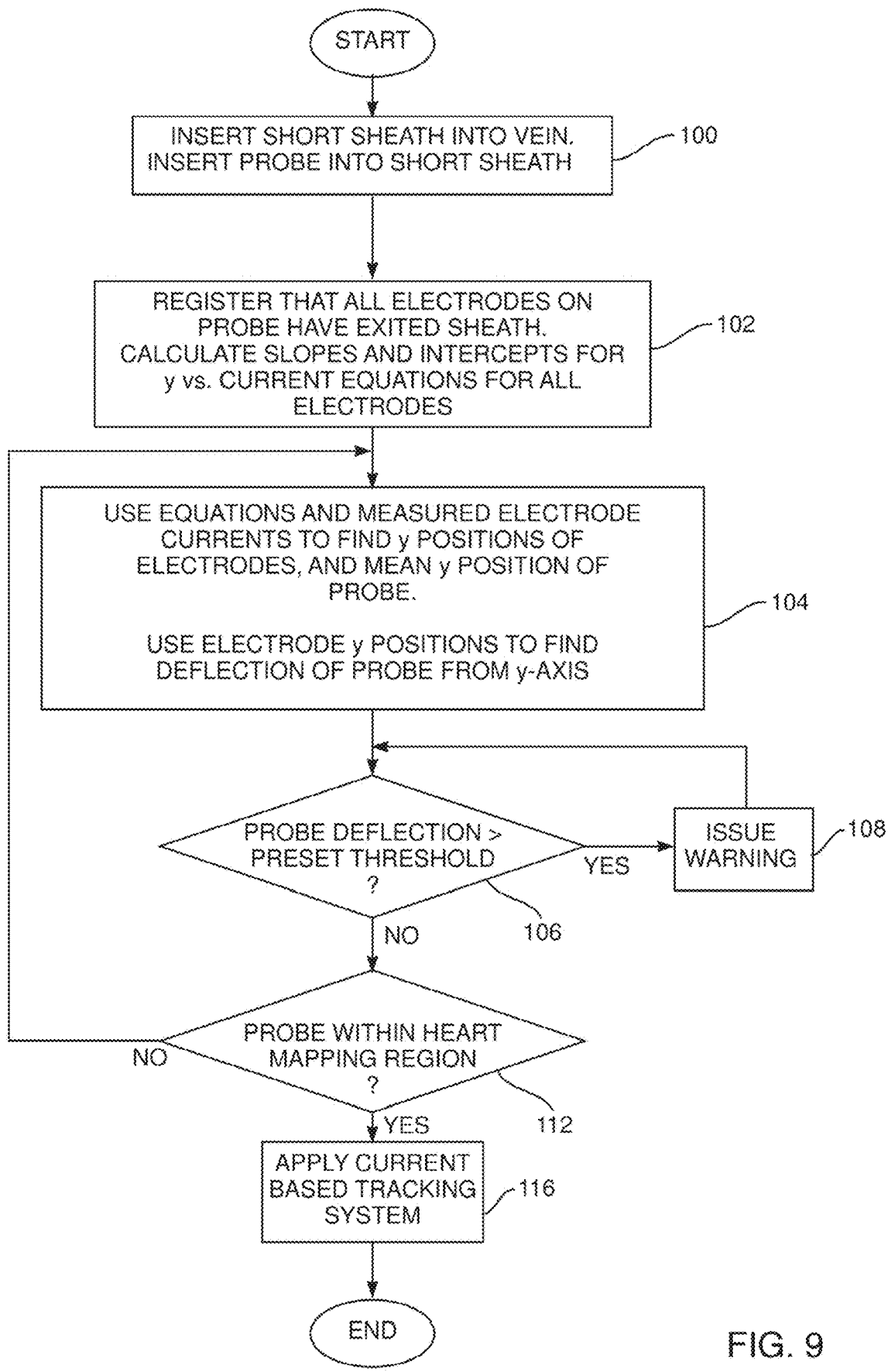
FIG. 9 is a flowchart of steps performed in tracking a probe in a patient.

FIG. 9 is a flowchart of steps performed in tracking a probe in a patient, and FIGS. 10-14 are diagrams illustrating aspects of the flowchart, according to an embodiment of the present invention. For clarity the flowchart assumes that the configuration of first modification 21A (FIG. 3) is implemented, with probe 32 of catheter 24 being inserted into patient 28. Except as otherwise stated below, first modification 21A is assumed not to include switch 73, so that patch 70 is always galvanically connected to patch 77C. By way of example, probe 32 is assumed to comprise three electrodes 50A, 50B, 50C, with electrode 50A being the most distal electrode and electrode 50C being the most proximal electrode. However, it will be understood that in embodiments of the present invention the probe may have two, or more than three, electrodes.

Figure 11:
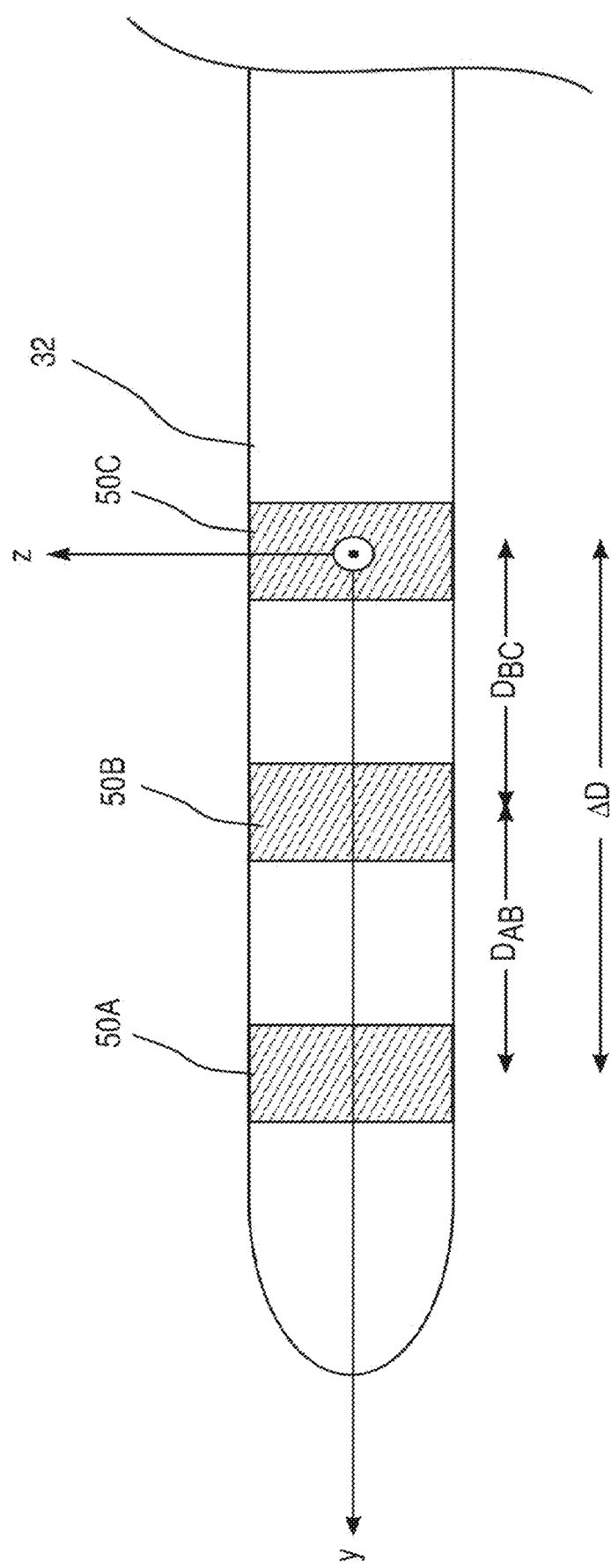

Probe 32 is assumed to be cylindrical, and prior to insertion into patient 28 the distances between electrodes 50A and 50B, and between electrodes 50B and 50C, are measured and recorded as $D_{AB}$ and $D_{BC}$, as shown in FIG. 11. A distance between the most proximal and most distal electrodes, $(D_{AB}+D_{BC})$, $\Delta D$, is also recorded. In addition, a value for a threshold current, $I_{thresh}$, the significance of which is described below, is input to processor 40. In one embodiment, $I_{thresh}$ is set at 450 µA, for a procedure wherein a current of 500 µA is injected into each electrode 50. However, those having skill in the art will be able to formulate other suitable values for $I_{thresh}$ without undue experimentation. As is explained below, in implementing the steps of the flowchart, the processor calculates values for M and B in equation (3).

In a first step 100, operator 22 inserts a short sheath into a femoral vein of patient 28, and then inserts probe 32 into the sheath. Processor 40 then begins measuring the currents received in channels C77 and calculates the normalized currents for each of electrodes 50A, 50B, and 50C. Initially, the normalized currents increase, as is illustrated in region A of the graph of FIG. 8.

Figure 10:
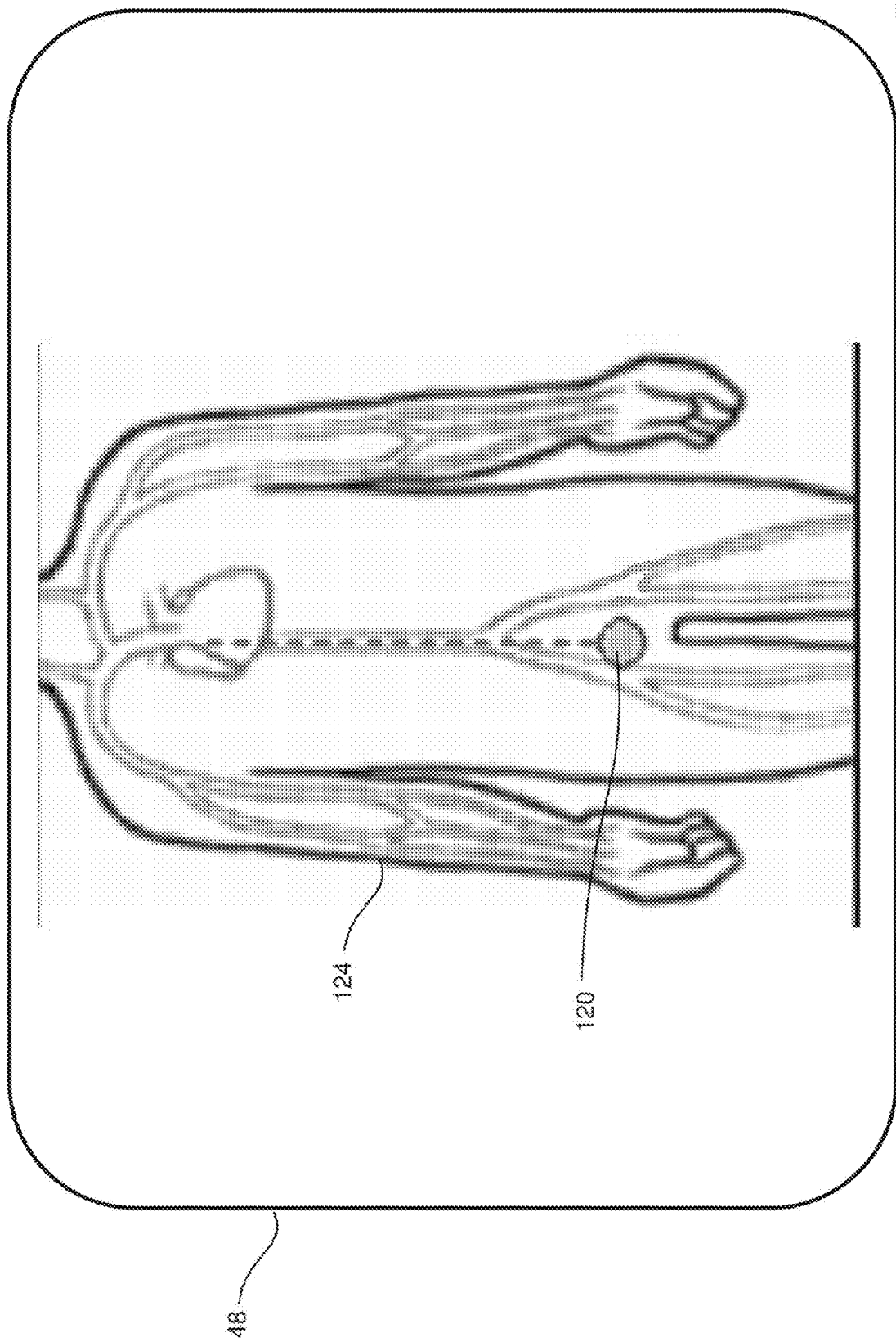
FIGS. 10-14 are diagrams illustrating aspects of the flowchart, according to an embodiment of the present invention.

In an exiting step 102, the processor registers when the currents, totaled for all patches 77, from all of electrodes 50A, 50B, and 50C, have become greater than threshold current $I_{thresh}$. At this point, the processor assumes that all the probe electrodes have exited the sheath. An indication that this point has been reached may be provided to operator 22, for example by the processor positioning a marker 120 on a generic FIG. 124 of a patient on display 48, as is illustrated in FIG. 10.

Upon the total current exceeding $I_{thresh}$, the processor records the normalized current values for the most distal electrode 50A, $I_{distal}$, and for the most proximal electrode 50C, $I_{proximal}$. The processor also records the normalized current values for any intermediate electrodes, in this case electrode 50B, herein termed $I_{50B}$. At this point, the probe is assumed to be aligned with the y-axis, the origin of which, for simplicity, may be placed at the most proximal electrode (which is adjacent to the distal end of the sheath), as is illustrated in FIG. 11.

The processor then calculates a value for the slope M in equation (3) using equation (4):

$$M = \frac{\Delta D}{I_{distal} - I_{proximal}} \quad (4)$$

where $\Delta D$ is the distance between the most distal electrode 50 and the most proximal electrode 50.

Using the value of parameter M from equation (4), processor solves for the value of B that best satisfies the three equations in Table I below. Alternatively, the processor may solve for B based on a subset of the equations in Table I.

TABLE I

| Electrode | Equation |
|---|---|
| 50C | $y_{50C} = 0 = M \cdot I_{N50C} + B$ |
| 50B | $y_{50B} = D_{BC} = M \cdot I_{N50B} + B$ |
| 50A | $y_{50A} = \Delta D = M \cdot I_{N50A} + B$ |

In a continue tracking step 104, processor 40 continually measures values of $I_{N50C}$, $I_{N50B}$, and $I_{N50A}$, as operator 22 pushes probe 32 further into the femoral vein. From the measured values at any given instance of time t during step 104, the processor calculates values of $y_{50C}$, $y_{50B}$, and $y_{50A}$—the respective y-positions of electrodes 50—using equation (3) with the values of M and B derived as described above. (The y-position of each electrode indicates the distance of the electrode from the sheath.) The processor averages the values of $y_{50C}$, $y_{50B}$, and $y_{50A}$ to find a mean y position $y_{mean}(t)$ for the probe at the time selected, as given by equation (5):

$$y_{mean}(t) = \frac{y_{50C} + y_{50B} + y_{50A}}{3} \quad (5)$$

Figure 12:
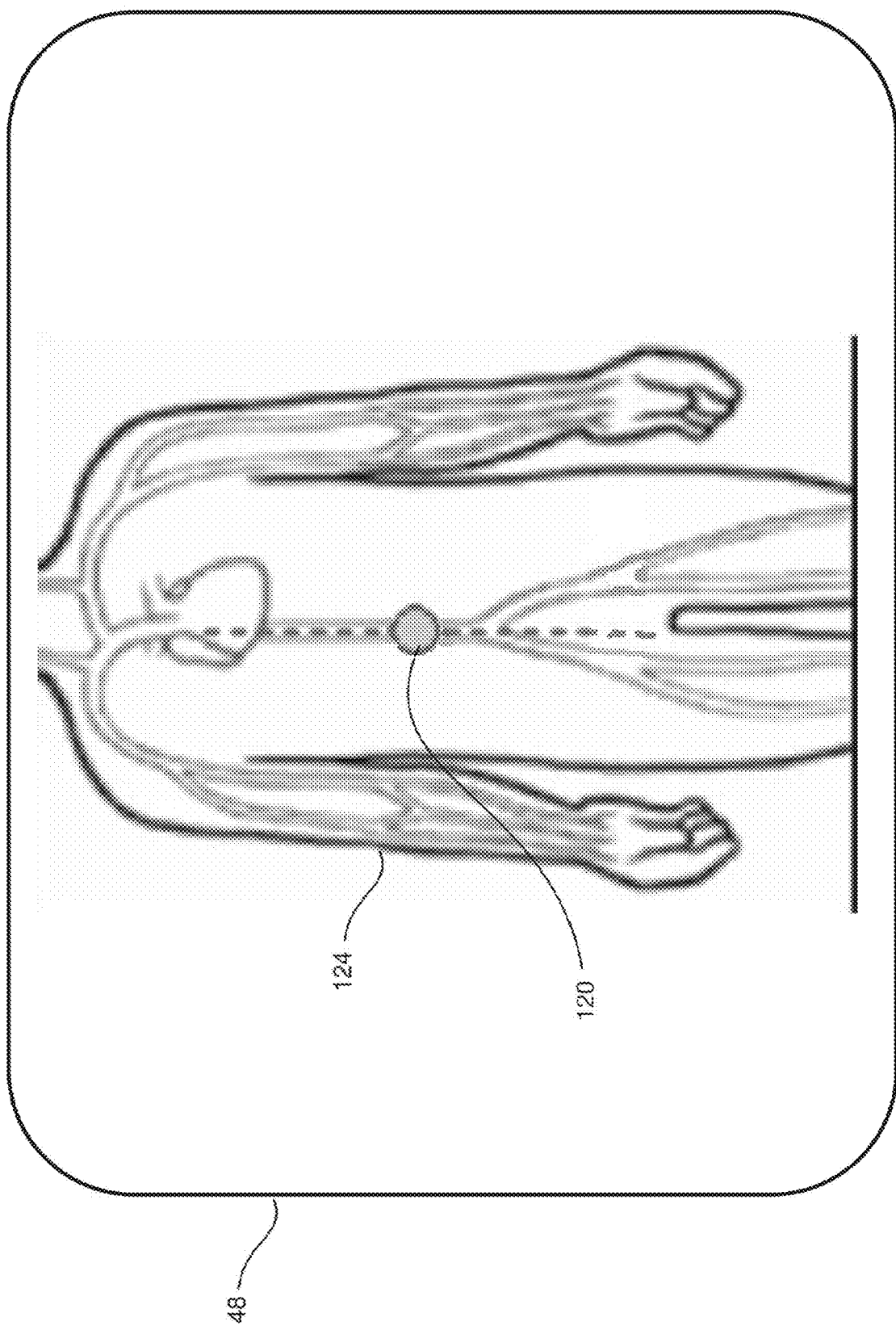

An indication that the position of the probe has reached a value of $y_{mean}(t)$ at the time selected may be provided to operator 22 by the processor moving marker 120 on the generic figure of the patient, to a position corresponding to $y_{mean}(t)$, as illustrated in FIG. 12.

While for clarity the description herein assumes that processor 40 uses linear relationships in the form of equations, those having skill in the art will appreciate that the processor may use other forms of linear relationships, such as a look-up table, and all such linear relationships are assumed to be comprised within the scope of the present invention. Thus, for example, given a normalized current, the processor may look up the corresponding y-position in a look-up table, rather than explicitly calculating the y-position using equation (3). The equation, look-up table, or other representation of the linear relationship may be referred to as a "linear function."

Figure 13:
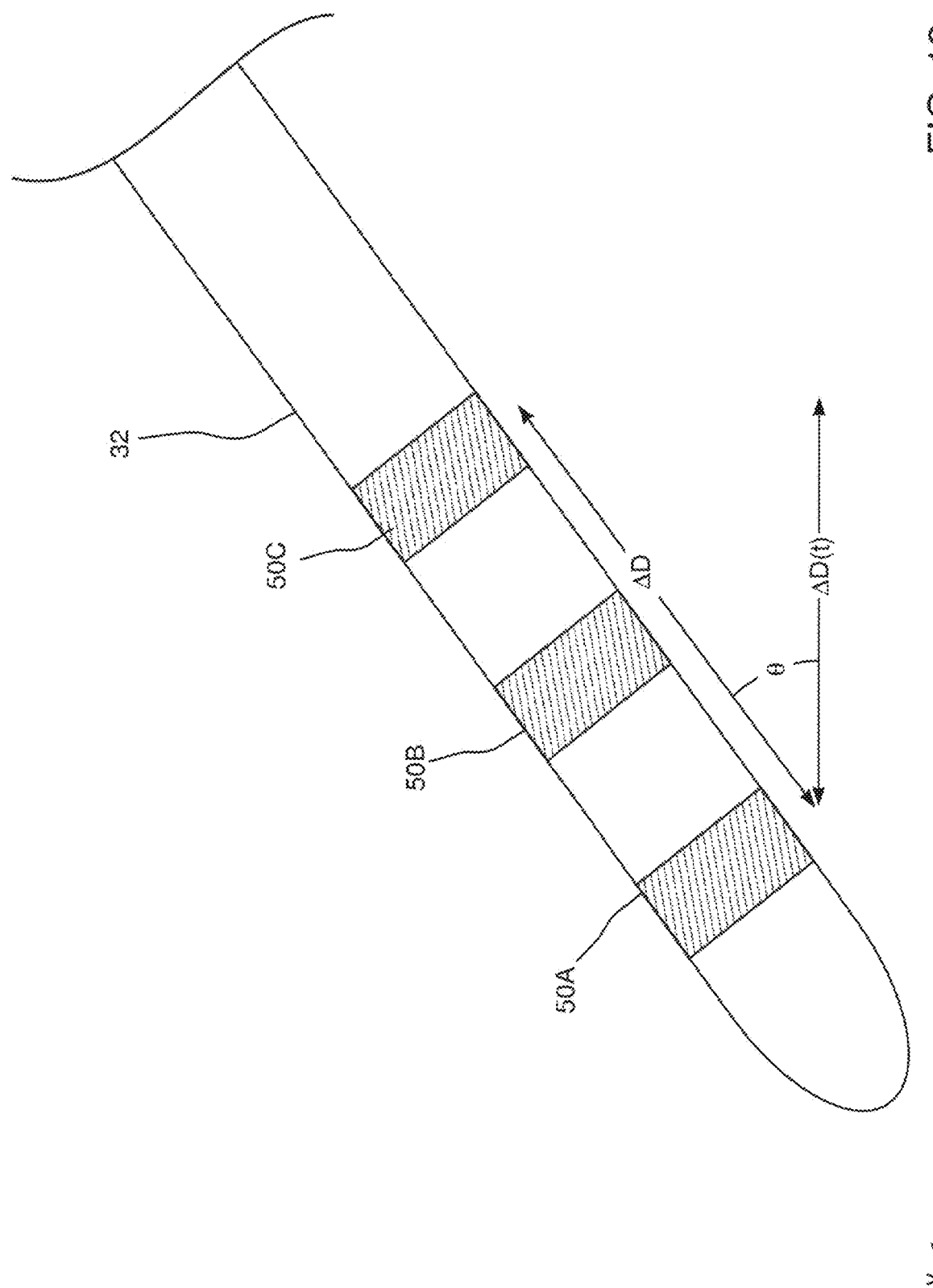

Also in step 104, the processor continually checks the deflection angle (or "deflection") θ of the probe relative to the y-axis defined in step 102, as illustrated in FIG. 13. The processor finds at any given time t a distance ΔD(t), parallel to the y-axis, between the most proximal and most distal electrodes, as given by equation (6):

$$\Delta D(t) = y_{50C} - y_{50A} \quad (6)$$

The processor then compares this distance with the value of ΔD (known from the initial measurements on electrodes 50C and 50A) to find deflection θ, according to equation (7):

$$\theta = \arccos \frac{\Delta D(t)}{\Delta D} \quad (7)$$

Figure 14:
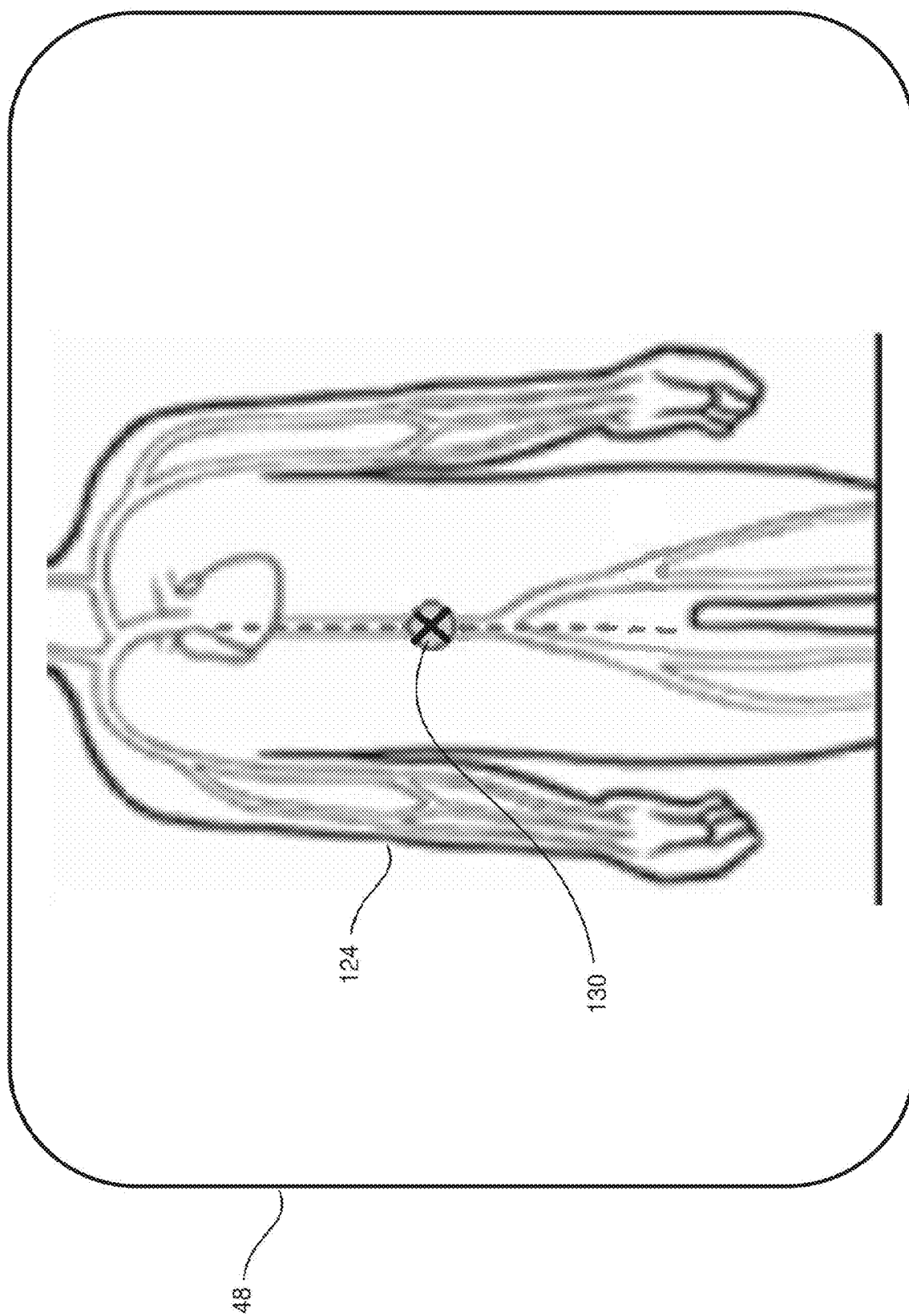

In a first comparison step 106, the processor checks if the deflection θ exceeds a preset threshold value, which in some embodiments is set at 45°. If the preset value is exceeded, the processor may issue a warning, in a warning step 108, to operator 22 that probe 32 may have deviated from the femoral vein (for example, by the probe having been inadvertently advanced into a vein communicating with the femoral vein). In one embodiment, the warning comprises a visual notification. For example, the processor may replace marker 120 with a different marker 130, as illustrated in FIG. 14. Upon receipt of the warning, operator 22 may manipulate the probe so that deflection θ does not exceed the preset value. Typically, after issuing a warning, the processor repeatedly performs first comparison step 106, and issues subsequent warnings (e.g., by continuing to show marker 130), until the necessary correction to the probe orientation has been made.

Upon first comparison step 106 returning negative, i.e., upon deflection θ not exceeding the preset value, control of the flowchart continues to a second comparison step 112, wherein the processor checks if probe 32 is within region 30 (FIG. 1). The check if probe 32 is within region 30 may be by any suitable method, such as, but not limited to, observing the currents on patch electrodes 77 relative to that on patch 77C (e.g., observing that the difference between the current on patch 77C and one of the other patches is less than a predefined threshold), and/or detecting that electrocardiograph (ECG) signals are present on one or more of electrodes 50 (assuming that mapping region 30 includes the heart), and/or using magnetic location if probe 32 has a magnetic sensor.

If second comparison step 112 returns negative, i.e., probe 32 is not in heart mapping region 30, control for the flowchart returns to step 104.

If second comparison step 112 returns positive, i.e., probe 32 is within region 30, an indication may be presented to operator 22 on display 48 that the probe is in the heart mapping region. In addition, in a final step 116 of the flowchart, processor 40 may stop tracking the (one-dimensional) y-position of the probe, and instead use the currents from all electrode patches 77 to track the (three-dimensional) position of the probe, using current based tracking system 21.

If switch 73 is present in line 71 (FIG. 3), then it is closed during steps 100-112, and is opened when control passes to final step 116. The closing and opening of switch 73 may be implemented manually by operator 22, and/or automatically by processor 40.

While the description above for the flowchart of FIG. 9 assumes for clarity that modification 21A is implemented to enable tracking of a probe, those having ordinary skill in the art will be able to modify the description, mutatis mutandis, if modifications 21B or 21C are implemented for tracking of the probe.

It will be appreciated by persons skilled in the art that the present invention is not limited to what has been particularly shown and described hereinabove. Rather, the scope of embodiments of the present invention includes both combinations and subcombinations of the various features described hereinabove, as well as variations and modifications thereof that are not in the prior art, which would occur to persons skilled in the art upon reading the foregoing description. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. A system for extending a tracking volume in a probe tracking system, the system comprising:
   multiple electrically-conductive channels; and
   a processor, configured to:
      receive, over the electrically-conductive channels, (i) respective first electric currents from a probe, which is within a body of a patient, via a plurality of first electrodes attached to skin of a patient at a mapping region of the patient's body, the mapping region defining the tracking volume, and (ii) a second electric current from the probe via a second electrode, which is attached to the skin at a second electrode location outside of the mapping region and is connected to one of the channels,
      ascertain respective first electric-current values of the first electric currents and a second electric-current value of the second electric current, and
      calculate a position of the probe between the mapping region and the second electrode, based on the first electric-current values and the second electric-current value, whereby the tracking volume is extended beyond the mapping region.

2. The system according to claim 1,
   wherein the mapping region includes at least part of a thorax of the patient,
   wherein the first electrodes are attached to the thorax, and
   wherein the second electrode is attached to a thigh of the patient.

3. The system according to claim 1, wherein the processor is configured to calculate the position of the probe by:
   calculating a normalized current-value $I_N = I_2/I_T$, $I_2$ being the second electric-current value and $I_T$ being a sum of the first electric-current values and the second electric-current value, and calculating the position of the probe by applying a linear function to $I_N$.

4. The system according to claim 3, wherein the processor is further configured to learn the linear function prior to applying the linear function, based on a plurality of initial electric currents received from the probe via the first electrodes and the second electrode.

5. The system according to claim 1, wherein the processor is further configured to:
   ascertain that the position of the probe is within the mapping first region, and in response to the ascertaining, disconnect the second electrode from the one of the channels.

6. The system according to claim 1, wherein the processor is further configured to calculate a deflection angle of the probe, based on the first electric-current values and the second electric-current value.

7. The system according to claim 1, wherein the first electrodes are patch electrodes, the second electrode is an additional patch electrode, the second electrode location is inferior to an insertion point at which the probe is inserted through the skin, and the second electrode is attached to the same electrically-conductive channel as one of the patch electrodes thereby creating a split patch providing a single current into the same electrically-conductive channel.

8. The system according to claim 1, further comprising an ablation-signal generator, and wherein the second electrode is a return electrode for the ablation-signal generator, the second electrode connected by a switch having at least a first position and a second position, wherein the first position selectively connects the second electrode to the ablation-signal generator and the second position selectively disconnects the second electrode from the ablation-signal generator and connects the second electrode to the same electrically-conductive channel as one of the patch electrodes thereby creating a split patch providing a single current into the same electrically-conductive channel.

9. The system according to claim 1, further comprising an ablation-signal generator, and wherein the second electrode is a return electrode for the ablation-signal generator, the second electrode connected by a first switch to the ablation-signal generator, and connected by a second switch to the same electrically-conductive channel as one of the patch electrodes thereby creating a split patch providing a single current into the same electrically-conductive channel.

10. A system for extending a tracking volume in a probe tracking system, the comprising:
a plurality of first electrodes, configured to, while attached to skin of a patient at a mapping region of a body of the patient and connected to different respective electrically-conductive channels, receive respective first electric currents from a probe disposed within the body, such that the first electric currents are passed over the channels, the mapping region defining the tracking volume;
a second electrode, configured to, while attached to the skin at a second electrode location outside of the mapping region, receive a second electric current from the probe; and
a switch, configured to connect the second electrode to a particular one of the channels, while the probe is between the mapping region and the second electrode, such that the second electric current is passed over the particular one of the channels, whereby the tracking volume is extended beyond the mapping region.

11. The system according to claim 10, wherein the switch is configured to connect the second electrode to the particular one of the channels by short-circuiting the second electrode to a particular one of the first electrodes.

12. The system according to claim 10, wherein the switch is further configured to connect the second electrode to an ablation-signal generator, instead of to the particular one of the channels, while the probe is in the mapping region.

13. The system according to claim 10,
wherein the switch is a first switch, and
wherein the system further comprises a second switch configured to connect the second electrode to an ablation-signal generator while the probe is in the mapping region and the second electrode is disconnected from the particular one of the channels.

14. The system according to claim 13,
wherein the first switch is disposed internally to a console, and
wherein the second switch is disposed internally to the ablation-signal generator.

15. A method for extending the tracking volume in a probe tracking system, the method comprising:
receiving, over multiple electrically-conductive channels, (i) respective first electric currents from a probe, which is within a body of a patient, via a plurality of first electrodes, which are attached to skin of the patient at a mapping region of the body, the mapping region defining the tracking volume, and (ii) a second electric current from the probe via a second electrode, which is attached to the skin at a second electrode location outside of the mapping region and is connected to one of the channels;
ascertaining respective first electric-current values of the first electric currents and a second electric-current value of the second electric current; and
calculating a position of the probe between the region and the second electrode, based on the first electric-current values and the second electric-current value, whereby the tracking volume is extended beyond the mapping region.

16. The method according to claim 15,
wherein the mapping region includes at least part of a thorax of the patient,
wherein the first electrodes are attached to the thorax, and
wherein the second electrode is attached to a thigh of the patient.

17. The method according to claim 15, wherein calculating the position of the probe comprises:
calculating a normalized current-value $I_N = I_2/I_T$, $I_2$ being the second electric-current value and $I_T$ being a sum of the first electric-current values and the second electric-current value; and
calculating the position of the probe by applying a linear function to $I_N$.

18. The method according to claim 17, further comprising learning the linear function prior to applying the linear function, based on a plurality of initial electric currents received from the probe via the first electrodes and the second electrode.

19. The method according to claim 15, further comprising:
ascertaining that the position of the probe is within the mapping first region; and
in response to the ascertaining, disconnecting the second electrode from the one of the channels.

20. The method according to claim 15, further comprising calculating a deflection angle of the probe, based on the first electric-current values and the second electric-current value.

21. A method for extending the tracking volume in a probe tracking system, the method comprising:
receiving, by a plurality of first electrodes attached to skin of a patient at a mapping region of a body of the patient and connected to different respective electrically-conductive channels, respective first electric currents from a probe disposed within the body, such that the first electric currents are passed over the channels, the mapping region defining the tracking volume;
receiving, by a second electrode attached to the skin at a second electrode location outside of the mapping region, a second electric current from the probe; and using a switch, connecting the second electrode to a particular one of the channels, while the probe is between the region and the second electrode, such that the second electric current is passed over the particular one of the channels, whereby the tracking volume is extended beyond the mapping region.

22. The method according to claim 21,
wherein the mapping region includes at least part of a thorax of the patient,
wherein the first electrodes are attached to the thorax, and
wherein the second electrode is attached to a thigh of the patient.

23. The method according to claim 21, wherein connecting the second electrode to the particular one of the channels comprises connecting the second electrode to the particular one of the channels by short-circuiting the second electrode to a particular one of the first electrodes.

24. The method according to claim 21, further comprising, using the switch, connecting the second electrode to an ablation-signal generator, instead of to the particular one of the channels, while the probe is in the mapping region.

25. The method according to claim 21,
wherein the switch is a first switch, and
wherein the method further comprises, using a second switch, connecting the second electrode to an ablation-signal generator while the probe is in the region and the second electrode is disconnected from the particular one of the channels.

26. The method according to claim 25,
wherein the first switch is disposed internally to a console, and
wherein the second switch is disposed internally to the ablation-signal generator.

27. A computer software product comprising a tangible non-transitory computer-readable medium in which program instructions are stored, which instructions, when read by a processor, cause the processor to:
receive, over multiple electrically-conductive channels, (i) respective first electric currents from a probe, which is within a body of a patient, via a plurality of first electrodes, which are attached to skin of the patient at a mapping region of the body, the mapping region defining a tracking volume, and (ii) a second electric current from the probe via a second electrode, which is attached to the skin at a second electrode location outside of the mapping region and is connected to one of the channels,
ascertain respective first electric-current values of the first electric currents and a second electric-current value of the second electric current, and
calculate a position of the probe between the region and the second electrode, based on the first electric-current values and the second electric-current value, whereby the tracking volume is extended beyond the mapping region.

* * * * *